(12) United States Patent
Wang et al.

(10) Patent No.: US 7,877,009 B2
(45) Date of Patent: Jan. 25, 2011

(54) METHOD AND SYSTEM FOR ELECTROCHEMICAL IMPEDANCE SPECTROSCOPY

(75) Inventors: Ding Wang, Austin, TX (US); Steven Y. Yu, Austin, TX (US); Gary A. Shreve, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 616 days.

(21) Appl. No.: 11/961,763

(22) Filed: Dec. 20, 2007

(65) Prior Publication Data

US 2009/0162076 A1   Jun. 25, 2009

(51) Int. Cl.
*H04B 10/00*   (2006.01)

(52) U.S. Cl. ............................... 398/9; 398/10; 398/16; 398/20

(58) Field of Classification Search ............... 398/9–38
See application file for complete search history.

(56) References Cited

U.S. PATENT DOCUMENTS

| | | | |
|---|---|---|---|
| 4,070,621 A * | 1/1978 | Bassen et al. ................. 324/96 |
| 4,380,763 A | 4/1983 | Peart et al. | |
| 4,780,664 A | 10/1988 | Ansuini et al. | |
| 4,849,753 A * | 7/1989 | Merry ..................... 340/854.7 |
| 4,962,360 A | 10/1990 | Homma et al. | |
| 5,195,046 A | 3/1993 | Gerardi et al. | |
| 5,301,001 A * | 4/1994 | Murphy et al. ............. 356/35.5 |
| 5,306,414 A | 4/1994 | Glass et al. | |
| 5,310,470 A | 5/1994 | Agarwala et al. | |
| 5,323,429 A | 6/1994 | Roarty et al. | |
| 5,338,432 A | 8/1994 | Agarwala et al. | |
| 5,367,583 A | 11/1994 | Sirkis | |
| 5,389,782 A * | 2/1995 | Hilliard ................. 250/227.17 |
| 5,397,896 A * | 3/1995 | Weiss et al. ................. 850/15 |
| 5,746,905 A | 5/1998 | Murray | |
| 5,859,537 A | 1/1999 | Davis et al. | |
| 5,929,990 A * | 7/1999 | Hall ........................... 356/519 |
| 5,963,034 A * | 10/1999 | Mahapatra et al. ....... 324/244.1 |

(Continued)

FOREIGN PATENT DOCUMENTS

EP   1 434 048 A1   6/2004

(Continued)

OTHER PUBLICATIONS

U.S. Appl. No. 11/613,670, filed Dec. 20, 2006 by inventors Wang et al., entitled "Detection System".

*Primary Examiner*—Agustin Bello
(74) *Attorney, Agent, or Firm*—Gregg H. Rosenblatt

(57) ABSTRACT

A method and system of measuring the spectroscopic impedance of a sensor and its immediate surroundings. The sensor is disposed on an engineered structure and is coated with a protective coating. The method includes providing a first optical signal having a first modulation frequency and amplitude. The method also includes transmitting the first optical signal and a second optical signal from a first location to a sensor location. The method also includes modulating the second optical signal with a second modulation frequency and amplitude, the second modulation frequency and amplitude converted from the first optical signal. The method also includes comparing the first modulation frequency to the second modulation frequency to determine one of a phase difference and a time lag and calculating the electrochemical impedance spectroscopy of the sensor and its immediate surroundings as a function of frequency.

19 Claims, 8 Drawing Sheets

U.S. PATENT DOCUMENTS

| | | | |
|---|---|---|---|
| 6,012,337 A * | 1/2000 | Hodge | 73/803 |
| 6,023,340 A * | 2/2000 | Wu et al. | 356/432 |
| 6,051,967 A | 4/2000 | Draaijer | |
| 6,054,038 A | 4/2000 | Davis et al. | |
| 6,063,486 A | 5/2000 | Kobayashi | |
| 6,144,026 A * | 11/2000 | Udd et al. | 250/227.14 |
| 6,173,091 B1 * | 1/2001 | Reich | 385/12 |
| 6,316,646 B1 | 11/2001 | Tacke et al. | |
| 6,320,137 B1 | 11/2001 | Bonser et al. | |
| 6,328,878 B1 * | 12/2001 | Davis et al. | 205/776.5 |
| 6,342,295 B1 | 1/2002 | Kobayashi | |
| 6,355,301 B1 | 3/2002 | Miller | |
| 6,384,610 B1 | 5/2002 | Wilson | |
| 6,399,939 B1 | 6/2002 | Sundareson et al. | |
| 6,445,565 B1 | 9/2002 | Toyoda et al. | |
| 6,531,694 B2 * | 3/2003 | Tubel et al. | 250/227.14 |
| 6,611,151 B1 * | 8/2003 | Ruedisueli et al. | 324/700 |
| 6,683,463 B2 | 1/2004 | Yang et al. | |
| 6,768,873 B1 * | 7/2004 | Palese | 398/140 |
| 6,805,788 B1 * | 10/2004 | Gonzalez-Martin et al. | 205/775.5 |
| 6,806,650 B2 * | 10/2004 | Johnson et al. | 315/111.21 |
| 6,896,779 B2 | 5/2005 | Thomas, III et al. | |
| 6,911,828 B1 * | 6/2005 | Brossia et al. | 324/649 |
| 6,977,379 B2 * | 12/2005 | Zhang et al. | 250/341.1 |
| 7,015,701 B2 * | 3/2006 | Wiegand et al. | 324/603 |
| 7,077,200 B1 * | 7/2006 | Adnan | 166/250.01 |
| 7,088,115 B1 * | 8/2006 | Glenn et al. | 324/691 |
| 7,117,742 B2 | 10/2006 | Kim | |
| 7,244,500 B2 | 7/2007 | Watts et al. | |
| 7,326,930 B2 * | 2/2008 | Crawely | 250/341.1 |
| 7,336,062 B2 * | 2/2008 | Mitrofanov | 324/96 |
| 7,450,053 B2 * | 11/2008 | Funk et al. | 342/22 |
| 7,450,996 B2 * | 11/2008 | MacDonald et al. | 607/115 |
| 7,504,834 B2 * | 3/2009 | Wang et al. | 324/693 |
| 2002/0078752 A1 | 6/2002 | Braunling et al. | |
| 2002/0153873 A1 | 10/2002 | Shapiro et al. | |
| 2002/0153874 A1 * | 10/2002 | Jiang et al. | 324/96 |
| 2004/0045365 A1 | 3/2004 | Richardson | |
| 2004/0047050 A1 | 3/2004 | Bauer et al. | |
| 2004/0189331 A1 | 9/2004 | Girshovich et al. | |
| 2005/0006251 A1 | 1/2005 | Thomas, III et al. | |
| 2005/0034985 A1 | 2/2005 | Zamanzadeh et al. | |
| 2005/0036135 A1 | 2/2005 | Earthman et al. | |
| 2005/0046860 A1 | 3/2005 | Waagaard et al. | |
| 2005/0082467 A1 | 4/2005 | Mossman | |
| 2006/0102343 A1 * | 5/2006 | Skinner et al. | 166/250.1 |
| 2007/0120572 A1 | 5/2007 | Chen et al. | |
| 2007/0144272 A1 | 6/2007 | Yu et al. | |
| 2008/0204275 A1 * | 8/2008 | Wavering et al. | 340/870.16 |
| 2009/0162076 A1 * | 6/2009 | Wang et al. | 398/185 |
| 2010/0115673 A1 * | 5/2010 | Kranz et al. | 850/30 |

FOREIGN PATENT DOCUMENTS

| | | |
|---|---|---|
| JP | 2002-022777 A | 1/2002 |
| JP | 2007-192837 A | 8/2007 |
| WO | WO 2004/031738 A1 | 4/2004 |
| WO | WO 2004/031739 A2 | 4/2004 |
| WO | WO 2004/065942 A1 | 8/2004 |

* cited by examiner

METHOD AND SYSTEM FOR ELECTROCHEMICAL IMPEDANCE SPECTROSCOPY

BACKGROUND

1. Field of the Invention

The present invention is directed to a detection method and system.

2. Related Art

Sensors capable of detecting corrosion are known, such as is described in U.S. Pat. Nos. 6,384,610; 6,328,878; 6,316,646; 5,859,537; 6,054,038; 6,144,026; 4,380,763; 4,780,664; 4,962,360; 5,323,429; 5,367,583; 6,445,565; and 6,896,779. For example, while some of these conventional approaches utilize "embeddable" corrosion sensors, the conventional technologies often employ rigid printed circuit boards and rigid silicon wafer chips. Limitations of such technology include thickness and fragility—placing rigid circuit boards under thin epoxy or paint coatings can cause disruptions in the coating, and silicon wafer-based sensors are prone to fractures, and do not conform to uneven surfaces.

Other corrosion detection systems have also been described in U.S. patent application Ser. No. 11/613,670 and U.S. Pat. Publ. No. 2007-0144272-A1.

SUMMARY OF THE INVENTION

According to a first aspect of the present invention, a method of measuring the spectroscopic impedance of a sensor and its immediate surroundings is provided. The sensor is disposed on an engineered structure and is coated with a protective coating. The method includes providing a first optical signal having a first modulation frequency and amplitude. The method also includes transmitting the first optical signal and a second optical signal from a first location to a sensor location. The method also includes modulating the second optical signal with a second modulation frequency and amplitude, the second modulation frequency and amplitude converted from the first optical signal. The method also includes comparing the first modulation frequency to the second modulation frequency to determine one of a phase difference and a time lag and calculating the electrochemical impedance spectroscopy of the sensor and its immediate surroundings as a function of frequency.

In one aspect, the transmitting step includes multiplexing the first optical signal with the second optical signal into a composite signal, the first optical signal being amplitude modulated and having a first wavelength, and the second optical signal being of continuous power and having a second wavelength different from the first wavelength. In a further aspect, the method includes splitting the composite optical signal into at least the first and second optical signals at the sensor location.

In another aspect, the modulating step includes modulating the second optical signal with a modulating device that is electrically connected to the sensor and that is powered by a signal that comprises an electrical conversion of the first optical signal.

In another aspect, the method further includes transmitting the modulated second optical signal to the first location and detecting the modulated second optical signal at the first location.

In another aspect, the calculating step comprises calculating the electrochemical impedance spectroscopy of the sensor and its immediate surroundings from the following equation:

$$R_C(\omega) = \frac{R_O(\omega)[P_0(\omega) - P_1(\omega)]}{P_1(\omega)}$$

where $R_O(\omega)$ is an initial impedance of the modulating device, where $P_0(\omega)$ is an initial optical response of the modulating device at the sensor location, and where $P_1(\omega) = Ae^{(i\Phi)}$, where A is the amplitude of the modulated second signal as is detected at the first location and wherein $\phi$ is one of the phase difference and the time lag. In another aspect, the electrochemical impedance spectroscopy is calculated over a range of frequencies from about 0.1 Hz to about 1 MHz.

According to another aspect of the present invention, a detection system for monitoring a physical condition of an engineered structure comprises a first sensor disposable on the engineered structure and disposable between a surface of the engineered structure and a protective coating substantially covering the surface, the first sensor including a modulation element. A controller is provided for retrieving data from the sensors, the controller including a comparator circuit and a signal generator to provide an AC signal at a frequency $\omega$. The detection system also includes one or more optical fibers coupling an optical signal generated by the controller to the first sensor, wherein the first sensor provides electrochemical impedance data corresponding to the engineered structure and protective coating.

In another aspect, the system includes a light source to generate the optical signal, wherein the optical signal comprises a first optical signal at a first wavelength having a first modulation frequency and amplitude, wherein the first modulation frequency and amplitude corresponds to the AC signal, and a second optical signal at a second wavelength, the second optical signal being of continuous power. In another aspect, the light source comprises first and second narrowband sources, wherein at least the first narrowband source is coupled to the signal generator.

In another aspect, the one or more optical fibers includes a first optical fiber to carry the first and second optical signals to the first sensor. Also, the one or more optical fibers can further comprise a second optical fiber to carry a return optical signal from the first sensor to the controller, the return optical signal comprising a modulated second optical signal, the second optical signal having a second modulation frequency and amplitude, the second modulation frequency and amplitude converted from the first optical signal.

In another aspect, the controller further comprises an optical multiplexer to combine the first and second optical signals into a composite signal, the first wavelength and the second wavelength being different. In yet another aspect, the controller further comprises a detector to receive and detect a return optical signal from the sensor.

In yet another aspect, the sensor comprises a sensor head having a patterned conductive element disposed on a flexible substrate mounted on the engineered structure and covered by a protective coating, and a modulating device electrically connected to the sensor head to receive the second optical signal. In another aspect, the sensor further comprises an optical signal demultiplexer, wherein the demultiplexer sends the first optical signal along a second optical path and sends the second optical signal along a first optical path. The sensor can further include a photodiode array disposed on the second optical path to convert the first optical signal into an electrical signal, wherein the modulating device is disposed along the first optical path, and wherein the modulating device is powered by the electrical signal from the photodiode array. In one aspect, the modulating device comprises an electro-chromic switch.

In yet another aspect, the engineered structure comprises one of a pipe and a girth weld portion of a pipe system.

The above summary of the present invention is not intended to describe each illustrated embodiment or every implementation of the present invention. The figures and the detailed description that follows more particularly exemplify these embodiments.

BRIEF DESCRIPTION OF THE DRAWINGS

The present invention will be further described with reference to the accompanying drawings, wherein.

Figure 1A:
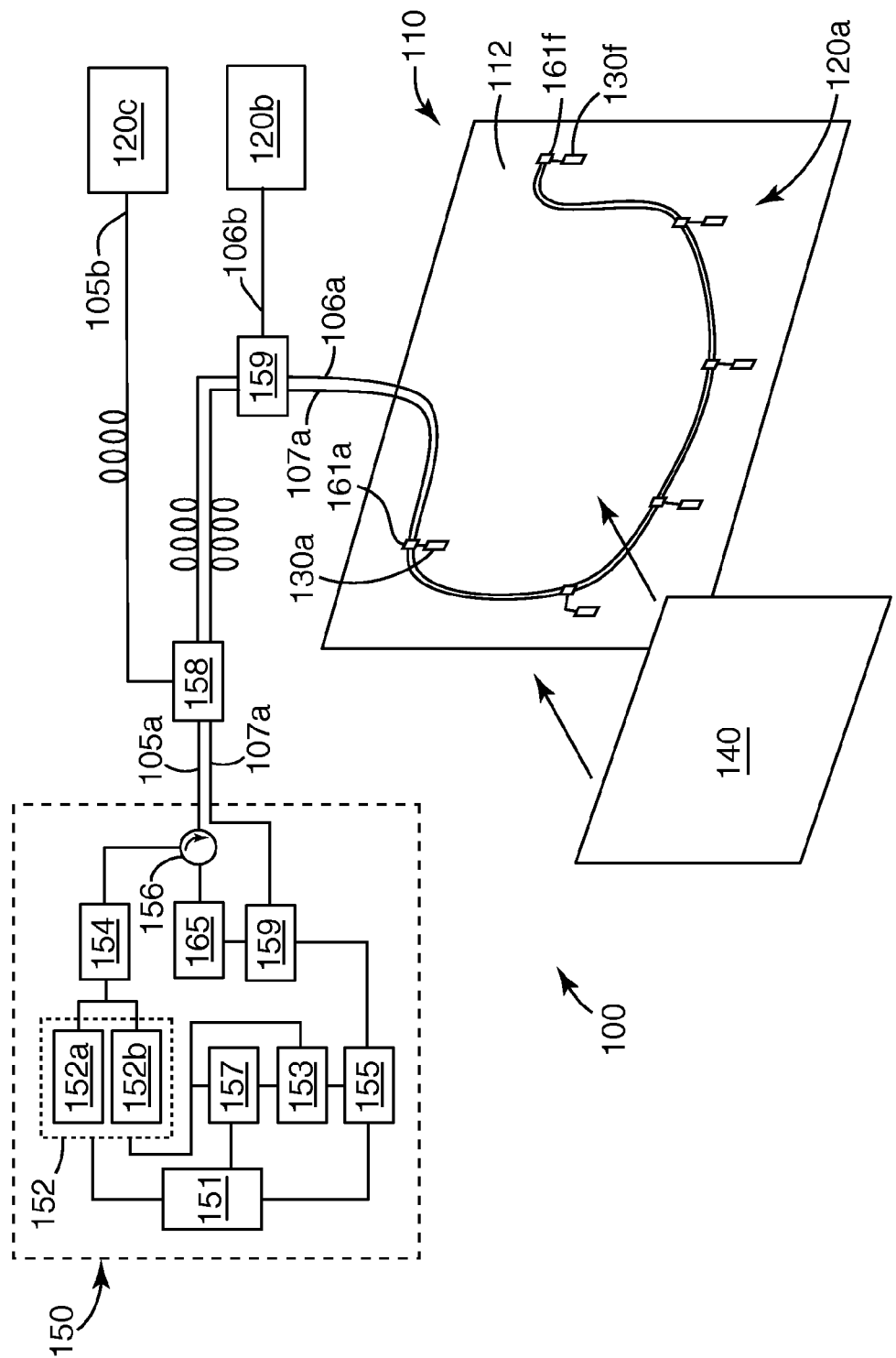
FIG. 1A is an exemplary detection system according to an aspect of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF THE EMBODIMENTS

The present invention is directed to a detection method and system. In particular, the detection method and system of the exemplary embodiments can be utilized to remotely detect the health of a coated surface on an engineered structure. In an exemplary aspect, the detection system utilizes an optical fiber backbone or network to link one or more arrays of detectors with a central control system to generate an electrochemical impedance spectroscopy (EIS) measurement that can be utilized by the central control system to provide real-time coating information for a particular engineered structure under test.

EIS is a testing method that has been used to characterize material and electronic properties by measuring the complex frequency dependence of voltage and current. The wide frequency range that can be used for measuring EIS response, 1 MHz to 0.001 Hz, leads to electromagnetic interference (EMI) challenges during testing when using electrical-based connection cables between the engineered structure and the test equipment. Other factors such as temperature variation can also affect an electrical signal carried by an electronic cable. In a preferred aspect, the test method and system are used to measure and collect EIS data by utilizing an optical network. An optical fiber based network, as is described in the exemplary aspects herein, is insensitive to EMI and the optical signals can propagate a long distance and carry EIS information back to the central station from an engineered structure without significant distortion.

In these exemplary implementations, the detection method and system can be configured to provide real-time, periodic (e.g. per hour, per day, per week) data related to one or more physical conditions of an engineered structure through a data acquisition system. This type of data acquisition system can provide real-time data for "condition-based" maintenance for engineered structures, as opposed to "preventive" maintenance, to help maximize the operational life of an engineered structure or object by providing data to better manage the scheduling of repairs or replacements of such objects or structures. In addition, the use of an optical backbone allows for a controller system to be located at a far distance (e.g., 1 km to 10 km or more, as measured by the length of the optical fiber transmission line) from the engineered structure being monitored.

According to an exemplary embodiment of the present invention, FIG. 1A shows a detection system 100 in schematic view. The detection system 100 includes a central control system, referred to as controller 150, linked to a sensor array 120a via a transmission optical fiber 105a. In this exemplary embodiment, sensor array 120a includes a plurality of sensors (in this example, a group of six (6) sensors (130a-130f) are shown for simplicity) coupled to a data transmission fiber 105a/106a. A return signal optical fiber 107a can also be employed in exemplary aspects. The sensor array 120a is disposed on a surface 112 of an engineered structure 110. In particular, as described in further detail below, the sensors of the sensor array can be configured to provide EIS information to the central controller. As is explained in further detail below, the embodiments of the present invention can also utilize different types of sensors.

In an exemplary embodiment, a coating 140 is applied to the surface 112 of the engineered structure 110. The sensors 130a-130f are configured to have a very thin design (e.g., having a sensing portion thickness of about 13 µm to about 75 µm) so that the sensors are easily disposed between the surface 112 and the coating 140. In this manner, the sensors can simultaneously provide data on the health of the coating 140 and the engineered structure 110.

The engineered structure 110 can be any type of structure or object that is exposed to natural elements, such as water, sea water, rain, wind, etc. The physical composition of the structure 110 can be a metal, such as steel, a carbon fiber composite, a ceramic, or a fiberglass-based material such as a fiberglass laminate.

Figure 5:
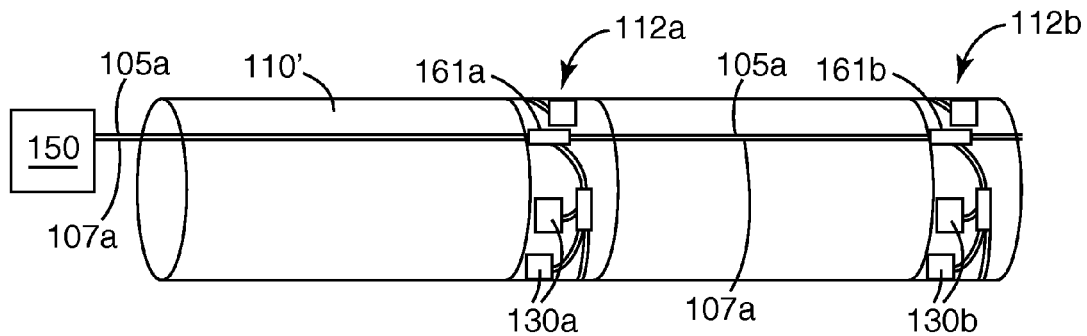
FIG. 5 shows an exemplary detection system implemented on a pipeline according to an aspect of the invention.

In an exemplary embodiment, the detection system 100 can be utilized in an oil/gas/water pipeline platform (see e.g., FIG. 5). For example, sensors can be distributed along the length of an above-ground or underwater/underground oil/gas/water pipeline that is difficult to visually inspect due to physical boundaries. The remote sensing attributes of embodiments of the present invention can provide a user the ability to query sensors from many kilometers away. Thus, the centrally located controller can remotely detect the health of the coatings and/or structures at various remote locations along the pipeline, especially at the many pipeline connection points, referred to as girth welds. As these numerous girth welds are each exposed to harsh environmental conditions, real-time, periodic coating and/or structure health assessments detected by exemplary detection system 100 can provide critical information related to maintenance planning.

For example, FIG. 5 shows an exemplary pipeline segment 110'. The pipeline segment is optically coupled to central controller 150 via an optical fiber 105a (and optionally a separate return fiber 107a), which transmit optical signals from and to the central controller. The pipeline segment 110' includes a plurality of sensor units, such as sensors 130a, 130b (only two are shown for convenience). In a preferred aspect, the sensors are disposed at various locations of the pipeline system. In this example, sensors 130a and 130b are disposed at girth welds 112a and 112b, respectively. As the girth weld portions of a pipeline are coated after the pipe units are welded together, these locations can be more susceptible to corrosion effects. In different aspects, each girth weld could include one or multiple sensors (e.g., a set of sensors wrapped around the girth weld). A series of tap-off devices 161a-161b can be used to tap off a portion of the optical signals originating at the central controller. Further details regarding the operation of these components are described below.

According to alternative embodiments, detection system 100 can be used with other types of engineered structures, such as marine platforms (e.g., ships or other vessels), tunnels, bridges, and aircraft, which are also susceptible to corrosion or other forms of physical deterioration.

To protect structure 110, coating 140 can comprise a coating, such as an epoxy-based coating or paint. For example, the coating can be a conventional fusion bonded epoxy (FBE) coating used for pipeline applications, such as is available from 3M Company, St. Paul, Minn. Other coatings can include polyamide epoxies and other coating epoxies (e.g., product no. 2216 A/B, available from 3M Company, St. Paul, Minn.). As is explained further below, detection system 100 can be used to detect health characteristics of coating 140.

In accordance with an exemplary embodiment, central controller 150 can be remotely located from the particular engineered structure 110 being monitored. In a preferred aspect, controller 150 includes a data acquisition system 151, a light source 152, a modulator 153, a signal generator 157 (which can be separate from or an integral part of modulator 153), and a comparator circuit 155. Other components can also include a multiplexer 154, a detector 159 and an optical circulator 156. In some aspects, the controller can also include an optical spectrum analyzer 165. In a preferred aspect, the controller 150 can determine the EIS response of the engineered structure 110.

In operation, one or more different optical signals can be generated by light source 152. The optical signal generated by the light source 152 is communicated to the sensor array 120a via a transmission optical fiber 105a. In a preferred aspect, the controller 150 sends and receives optical signals. The return optical signals can be directed to the central controller by a separate return fiber 107a or by the transmission fiber 105a. In some aspects, the return signals can be fed directly into detector 159. In other aspects, the return signals can be directed by the optical circulator 156 to the detector 159 or (optionally) the spectrum analyzer 165. Optionally, an optical switch 158, controlled by the controller 150, can be utilized to distribute the optical signal to other engineered structures and/or other sensor arrays, such as sensor array 120c. The use of one or more optical signals to communicate with the one or more sensor arrays of the overall system provides for long distance connections and a substantial reduction or elimination of electromagnetic interference (EMI) signal degradation that would be present in an electrical wire-based network.

In one aspect, data acquisition system 151 can be configured as a server or other computer-based device that communicates with light source 152, (optionally) modulator 153, (optionally) signal generator 157, comparator circuit 155, and (optionally) optical switch 158. Data acquisition system 151 can include an interface device and a computer for data storage and display. For example, the data acquisition system can include a computer with an interface card (e.g., a GPIB card) to communicate with the signal generator/modulator and comparator circuit. Also, the data acquisition system can be coupled to a separate display to provide graphical data, such as real-time coating condition data, to a user. As the data acquisition system 151 can be a computer, server, or computer-based device, data collection, manipulation, analysis, and delivery can be provided via application-specific software programs loaded thereon. Similar data retrieval, decoding and storing processes can be utilized for all sensors or sensor groups used in the system. If a sensor indicates that a degradation of coating or structure has occurred, an alert can be provided to the user (e.g., in audible and/or visual format). Otherwise, data can be displayed upon user request. An automated process can be employed to activate data retrieval and analysis in a real-time, periodic manner.

In one aspect, for EIS measurements, light source 152 comprises one or more distinct, (relatively) narrowband sources, with each having an output at a different wavelength, yielding an output signal of light having multiple separate wavelength channels $\lambda_1$-$\lambda_n$. For example, the set of narrower band sources can comprise a set of lasers or a set of diode sources, such as laser diodes or LEDs, each having a different output wavelength $\lambda_1$-$\lambda_n$. For example, diodes having different wavelength outputs of $\lambda_1$-$\lambda_n$ (e.g., 1550 nm, 1550.5 nm, 1551 nm, . . . 1570 nm) can be used separately. As shown in FIG. 1A, exemplary light source 152 can include separate sources 152a and 152b. The separate wavelength signals generated by sources 152a and 152b can be multiplexed by multiplexer 154 and transmitted along fibers 105a, 106a. In this type of system, the two signals can be used to query all of the sensors in the system. In a further alternative, light source 152 can include one or more tunable lasers that produce laser outputs at a wider wavelength range (e.g., with laser output spanning a 10-20 µm range). In yet a further alternative, light source 152 can include one or more continuous broadband sources (e.g., lamps), with a (relatively) low spectrum power density. For example, a source such as an amplified spontaneous emission source can also be used.

In a preferred aspect, a modulator 153 and/or signal generator 157 can provide an AC signal to modulate one or more of the optical signals generated by light source 152. The modulated signal (AM) is transmitted out to the remote sensors. In one aspect, signal generator 157 can be an AC signal generator, where the AC output signal can be amplified with an external power amplifier to add a DC bias, with the resultant biased AC signal being applied to the optical modulator 153, which modulates the output of the light source in a controlled manner. In one aspect, laser source 152a outputs a first optical signal at a wavelength $\lambda_1$, whereas laser source 152b outputs a second optical signal at a wavelength $\lambda_2$. The first laser source can be coupled to the modulator 153 so that the optical signal $\lambda_1$ can be modulated at a frequency $\omega$, whereas the second laser signal $\lambda_2$ is not modulated (or vice versa). During impedance measurements, the frequency $\omega$ can be varied (e.g., from 0.001 Hz-1 MHz, or more preferably 0.1 Hz to 1 MHz) so that complete spectroscopic measurements can be undertaken. Other frequency sweeps can also be utilized.

The multiplexed signal can then be transmitted along fiber 105a. In one aspect, fiber 105a can carry transmitted signals and return signals. In an alternative aspect, return signals can be carried on a separate fiber backbone, such as fiber 107a. As would be understood by one of ordinary skill in the art given the present description, for a multiple wavelength light source 152, several optical signals of different wavelengths can be modulated while several other optical signals are not modulated. As described further below, comparison of the information associated with the transmitted and returned signals can provide the basis for making EIS measurements.

The multi-wavelength optical signal is transmitted to a first sensor array 120a along optical fiber 105a. Optical fiber 105a can be a conventional telecommunications fiber, such as a SMF28™ Optical Fiber available from Corning, Inc. (Corning, N.Y.) or a different optical fiber that is operational at a wavelength region outside the typical optical telecommunication wavelength regions 1300 nm or 1550 nm. Optionally, the optical signal can be further distributed to an additional sensor array 120b via switch 169. If a return fiber (e.g., fiber 107a) is used, the construction of the return fiber can be the same as the transmission fiber.

As shown in the embodiment of FIG. 1A, the optical signal (having wavelengths $\lambda_1$-$\lambda_n$) that is received at sensor array 120a can be distributed to the individual sensors 130a-130f via a series of tap-off devices 161a-161f. In a preferred aspect, tap-off device 161a can comprise a demultiplexer, which distributes a portion of the incoming signal (e.g., first and second optical signals $\lambda_1$, $\lambda_2$) to sensor 130a, while the remaining signal $\lambda_3$-$\lambda_n$ is distributed to the other sensors of the array, sensors 130b-130f.

Figure 1B:
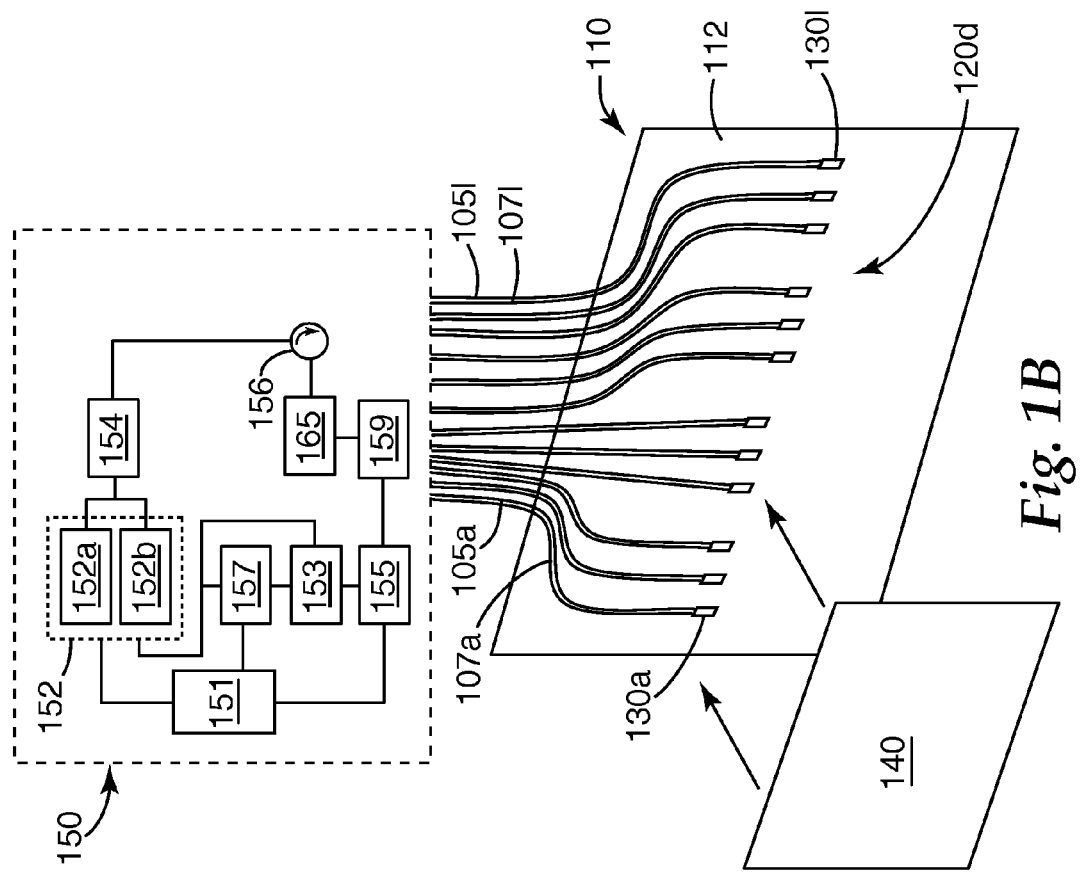
FIG. 1B is an exemplary detection system according to an alternative aspect of the present invention.

In an alternative embodiment, as shown in FIG. 1B, sensor array 120d can comprise a plurality of individual sensors (in this example, sensors 130a-130l). Here, each individual sensor is coupled directly to the controller 150 (e.g., through optical fibers 105a-105l, and optionally, return fibers 107a-107l). Here, return signal fibers (not shown) can also be employed. In this alternative aspect, tap-off devices (such as tap-off devices 161a-161f) are not necessary.

Figure 2:
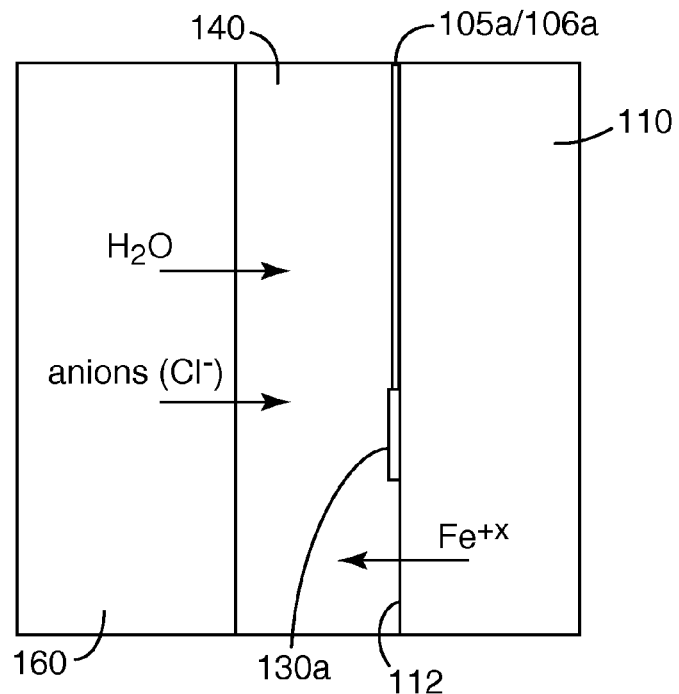
FIG. 2 is a cross-section view of a sensor embedded between a coating and an engineered structure according to an exemplary aspect of the present invention.

As shown in the cross-section view of FIG. 2, a sensor 130a can be disposed on surface 112 of structure 110. Sensor 130a can be secured to surface 112 via an adhesive, such as a moisture resistant 2-part epoxy (e.g., a Tra-Con 2151 adhesive, available from Tra-Con Corp., Bedford, Mass.), or a double-sided tape or transfer adhesive, such as 3M VHB, available from 3M Company, St. Paul, Minn. Sensor 130a can communicate to the central controller 150 via optical fibers 105a/106a and (optionally) return fiber 107a. Coating 140 is applied to the surface 112 to protect the structure 110 from the corrosive effects of an external substance or material 160. As is explained in more detail below, sensor 130a can detect the health of the coating 140 (e.g., monitoring the impedance), which indicates general coating health as coating 140 deteriorates and as structure 110 starts to corrode.

Figure 3A:
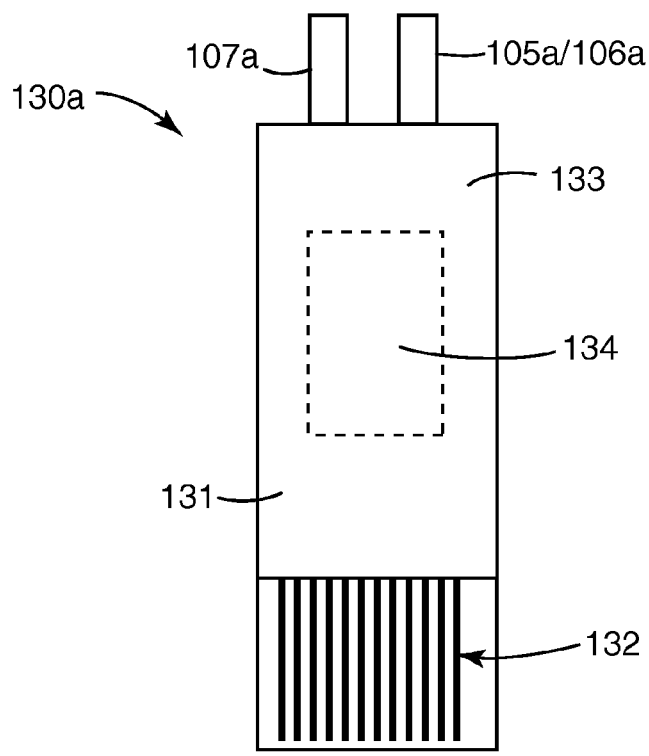
FIG. 3A is an exemplary sensor according to an aspect of the present invention.
Figure 3B:
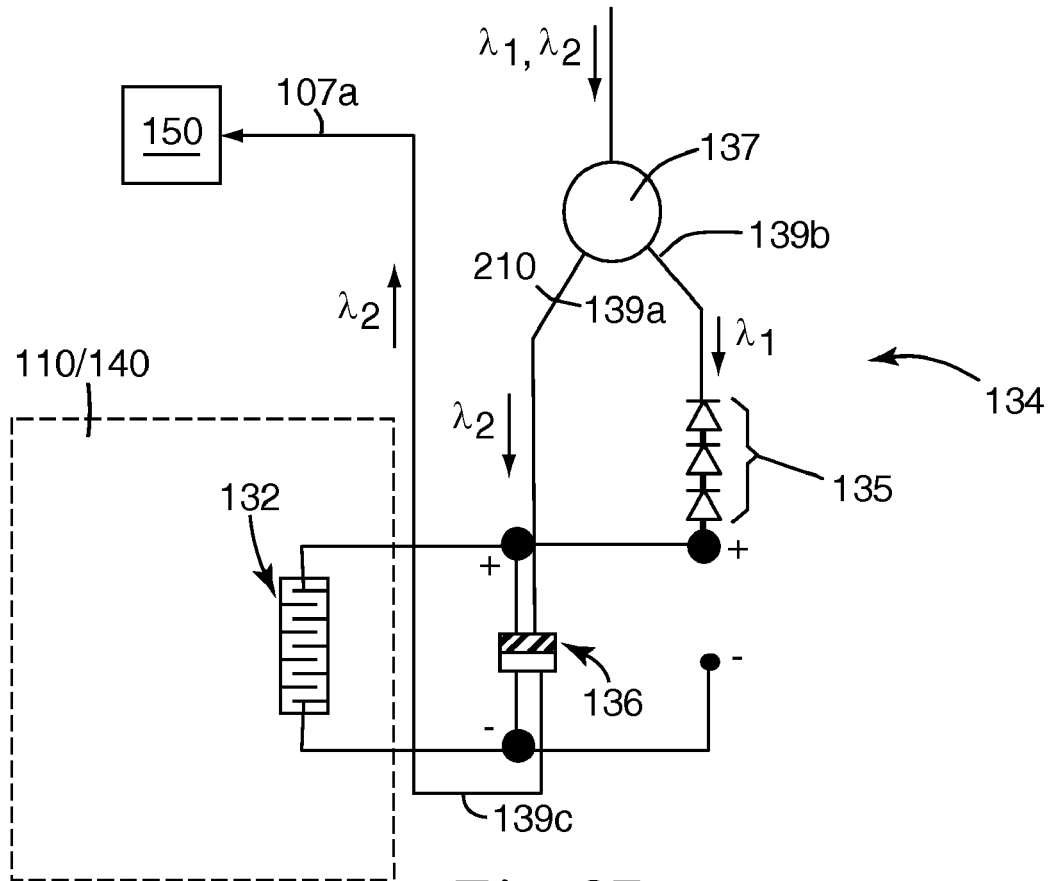
FIG. 3B is a schematic diagram of a portion of an exemplary sensor according to another alternative aspect of the present invention.

As shown in FIG. 1A, sensor array 120a can include several individual sensors 130a-130f. Of course, a greater number of sensors or a fewer number of sensors can be utilized in sensor array 120a, depending on the size of the engineered structure or the particular application. In a preferred aspect, each individual sensor can have the same basic structure. For example, as shown in FIGS. 3A and 3B, sensor 130a can be formed on a flexible polyimide substrate (described in more detail below) and can include an optoelectronic interface 134 disposed thereon. Alternatively, individual sensors can have different structures.

In one aspect, the optoelectronic interface 134 can be disposed on a base material, such as a polymer-based material, e.g., a polyamide, polyester, liquid crystal polymer or an acrylic material. The base material can provide support for the optoelectronic interface 134 and/or part of a hermetic seal with a cap portion (not shown). The base material and/or other portions of the sensor may be adhered to the surface of the engineered structure 110 by an adhesive, such as VHB adhesive available from 3M Company (St. Paul, Minn.). A protective coating or encapsulant 133 can also be provided to protect the components and interconnects from exposure. Optionally, for further protection, a package cap material, such as a hard plastic, can provide an outer protective shell. The overall package thickness can be kept to about 100 µm to about 1000 µm.

The optoelectronic interface 134 can include an optical signal demultiplexer 137 (see FIG. 3B). In one aspect, the demulitplexer 137 can comprise a thin film-based channel selector that selects a predefined channel or channels (e.g., $\lambda_1$, $\lambda_2$). Moreover, the optical signal demultiplexer of each sensor can be used to identify each individual sensor by its wavelength $\lambda_n$. The optical signal demultiplexer 137 can be used to split the optical signals in two paths, e.g. paths 139a and 139b, as is shown in FIG. 3B. In one aspect, demulitplexer 137 selects a signal $\lambda_2$ and sends it along path 139a, while the signal $\lambda_1$ is sent along path 139b.

Sensor 130a can further include a PIN diode array 135, preferably a photo-voltaic PIN diode array, to receive and convert a portion the optical signal into electrical power. As shown schematically in FIG. 3B, the signal $\lambda_1$ is sent along path 139b to the PIN diode array 135, which receives the optical signal and generates electrical power. In a preferred aspect, as signal $\lambda_1$ is modulated at the central controller at a frequency ω, the electrical signal generated by PIN diode array 135 will also be modulated at the frequency ω. The electrical power can be used as a power source for a modulating device, in this exemplary aspect, an electro-chromic switch 136. As the signal $\lambda_1$ is modulated, the modulated electrical signal from the diode array will also provide a modulated power source for the electro-chromic switch 136. In this exemplary aspect, the signal $\lambda_2$ is sent along path 139a to the electro-chromic switch 136. The electro-chromic switch 136 receives the second optical signal $\lambda_2$ and modulates the previous DC signal so that the return signal for $\lambda_2$ that is carried on path 139c is modulated.

As is described below, the amount of power available to the modulating device (electro-chromic switch 136) can depend on the condition of the protective coating 140, as the sensing portion 132 is coupled to the power source for the electro-chromic switch 136.

Figure 3C:
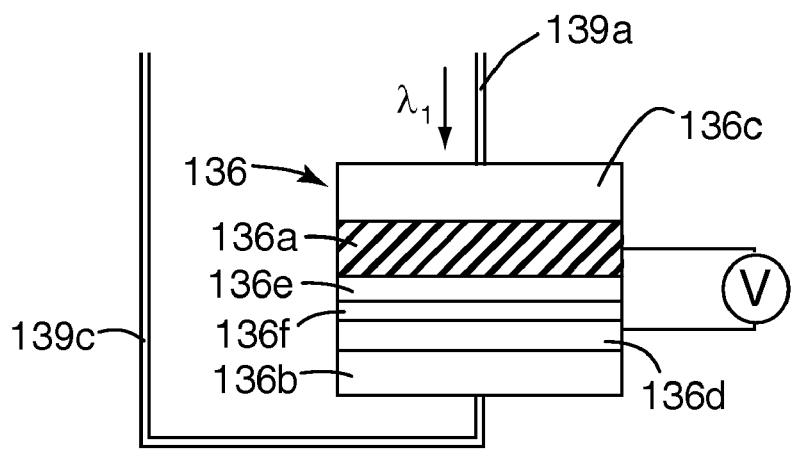
FIG. 3C is a schematic view of the electro-chromic switch of FIG. 3B.

As shown in FIG. 3C, an exemplary electro-chromic switch 136 can include two optically transmissive materials 136c, 136d having a voltage-sensitive material 136a disposed therebetween. Voltage-sensitive material 136a can comprise, e.g., tungsten trioxide. An electrolyte, 136e is disposed between the voltage sensitive material and layer 136f, preferably a vanadium pentoxide layer. Electrolyte layer 136e provides a charge transfer mechanism for the applied voltage V, where the vanadium pentoxide layer 136f can enhance the contrast ratio during the modulation of the electro-chromic switch. In one aspect, an optically transmissive substrate 136b can be provided that is coupled to a return signal fiber 139c (and to return signal fiber 107a). In an alternative aspect, transmissive material 136d can be coated with a highly reflective coating in place of substrate 136b, thus providing a return signal reflected back through the modulator.

In another aspect, the modulating device can comprise a micro-electro-chromic switch. The details of manufacturing a fiber based micro-electro-chromic switch and the components thereof, are described in pending U.S. patent application Ser. No. 11/613,670, incorporated by reference herein in its entirety. The micro-switch that is particularly described in the pending patent application Ser. No. 11/613,670 is most appropriate for reflecting the return signal back to the central controller. In an alternative aspect, such a micro-electro-chromic switch can be modified for use in optical system that includes a return fiber (e.g., by removing the back reflector and attaching a return fiber). Such a system can have an extremely compact structure formed on the terminal end of an optical fiber or formed between the terminal ends of a transmission fiber and a return fiber.

Sensor 130a further includes a sensor portion 132. In a preferred aspect, array sensing portion 132 can include an electrode structure having interdigitated metal-based (e.g., gold, silver, copper) circuits, which can be used as anodes and cathodes for electrochemical/corrosion measurements, and can be formed on a flexible polyimide substrate. In addition, a portion of sensor 130a can be coated with its own protective overcoat 133 (e.g., covering the electrical/optical conversion portion of the sensor, but leaving sensing portion 132 exposed to the structure 110 and coating 140).

In an exemplary embodiment, sensing portion 132 is formed on a thin, flexible substrate material, such as 3M's flexible circuit material, available under the trade name 3M™ Flex, from 3M Company, St. Paul, Minn. An exemplary article and process for making such a flexible circuit are described in U.S. Pat. No. 6,320,137, incorporated by reference in its entirety. By "flexible", it is meant that the sensor and (if applicable) substrate can be bent so that the sensing portion does not delaminate (e.g., the sensing portion can undergo 90 degree (or greater) bend at a very small radius of curvature, or even a sharp right angle or being creased, without losing its conductive qualities).

For example, the sensing portion 132 can include a substrate, such as a polyimide material. The sensor electrode structure can be formed as a patterned multilayer material upon substrate having, for example, a chrome tie layer, a copper (or other conductive) layer disposed thereon, and a silver (or gold or other metal) layer disposed on the copper layer. Other multi-layer structures can be utilized, as would be apparent given the present description. Thus, a sensing portion 132 with an exemplary cathode-anode structure can provide the ability to measure the impedance between the cathode and anode, at previously difficult-to-monitor locations.

In an alternative embodiment, the sensing portion 132 can be configured as an electrode formed of a chemical species that is sensitive to water, such as Al, Fe, or Zn. When the chemical species interacts with water, there will be a change in the measured impedance or resistance. Other corrosion sensitive species can also be utilized, as would be apparent to one of ordinary skill in the art given the present description.

In operation, in one aspect, the modulating device, electro-chromic switch 136, is powered by the output of PIN diodes 135. As shown in the schematic diagram of FIG. 3B, the sensing portion 132 preferably has a physical construction of an electrode structure having interdigitated metal-based circuits formed on a flexible polyimide substrate. In a preferred aspect, the electrochromic switch 136 is placed in parallel with the interdigitated sensing portion 132. Alternatively, the electrochromic switch 136 can be placed in series with the interdigitated sensing portion 132.

For example, at the initial stages, the quality of coating 140 is good. Accordingly, the resistance/impedance due to sensing portion 132 is high. As a result, applying an AC voltage (V) across the electro-chromic switch 136 under these initial conditions produces an AC voltage signal with a large amplitude. When the AC voltage (V) across the electro-chromic switch 136 has a large amplitude, the voltage-sensitive material 136a modulates the incoming signal ($\lambda_2$) with a (relatively) large amplitude modulation, so that the amplitude (A) of the return $\lambda_2$ signal back to the controller 150 is high.

At later stages, after exposure to corrosive elements, the quality of coating 140 deteriorates. Accordingly, the resistance/impedance due to sensing portion 132 is decreased. As a result, the AC voltage (V) across the electro-chromic switch 136 has a smaller amplitude. When the AC voltage (V) across the electro-chromic switch 136 has a smaller amplitude, the voltage-sensitive material 136a modulates the incoming signal ($\lambda_2$) with a smaller amplitude, so that the return $\lambda_2$ signal has a (relatively) smaller amplitude (A). Thus, the operator can determine the relative health of the coating 140 at a remote location. Other variations of this operation can also be utilized, as would be apparent to one of ordinary skill in the art given the present description.

While the above description is limited to the $\lambda_1$, $\lambda_2$ signals, aspects of the invention are not limited, as $\lambda_3$, $\lambda_4$ signals can be sent to sensor 130b, $\lambda_5$, $\lambda_6$ signals can be sent to sensor 130c, and so on. Thus, in a preferred aspect, other signals ($\lambda_3$-$\lambda_n$) at other sensors locations (130b-130n) are generated corresponding to the coating health at the other locations of the engineered structure. Thus, a spectrometer device, such as an optical spectrum analyzer 165 can be used at the controller to analyze the return light signals. Alternatively, the central controller can utilize one or more demultiplexers (not shown) to separate the return signals as a function of wavelength.

In a preferred aspect, as the modulated $\lambda_2$ signal returns to the central controller 150 via return fiber 107a, the amplitude of the $\lambda_2$ signal is measured and the phase characteristics of this return signal can be compared against the AC signal used to modulate the $\lambda_1$ signal, thus providing the necessary data to determine an accurate EIS measurement. For example, the modulated $\lambda_2$ signal returns to the central controller 150. In one aspect, the return signal is provided on return fiber 107a and is directed to the detector 159. In an alternative aspect, the return signal can reach the central controller via fiber 105a and can be directed to the detector 159 via the optical circulator 156.

The modulated return $\lambda_2$ signal is converted to an electrical signal by detector 159, which preferably comprises one or more sets of PIN photodiodes, such as photo-voltaic diodes. This modulated, electrical signal is fed to the comparator circuit (e.g., which includes a digital lock-in amplifier, such as is commercially available). Comparator circuit 155 includes a set of inputs, at least two of which include an input for the converted signal from detector 159 and an input from the signal generator 157 and/or modulator 153. These signals can be compared using a lock-in amplifier or the like to determine the phase difference or time delay. The measured signals can then be fed to the main controller circuit 151 to calculate the EIS measurement for the particular sensor or sensors. For full EIS testing, the frequency of the modulator/signal generator can be varied (e.g., sweeping through frequencies $\omega_1$, $\omega_2$, $\omega_3$, and so on) and the measurements taken at different frequencies.

In further detail, in a preferred aspect, an EIS measurement of an engineered structure utilizing the above-described system can be undertaken as follows.

At the central controller 150, a modulated AC signal (t1), having a frequency $\omega$, can be generated by the signal generator 157/modulator 153. This modulated signal is fed to light source 152 such that at least one output signal (e.g., $\lambda_1$) of light source 152 is an AM optical signal having a frequency $\omega$. For full spectroscopic coverage, the a frequency $\omega$ can be swept over a wide range of frequencies (in one aspect, from 0.001 Hz to 1 MHz, or, in another aspect, from 0.1 Hz to 1 MHz or less). The AM $\lambda_1$ signal is combined with at least one non-modulated (preferably DC) optical signal (e.g., $\lambda_2$) by a multiplexer and the composite signal is sent to at least one remotely located sensor or sensor array disposed on the engineered structure (e.g., sensor array 120a) via an optical transmission line, such as fiber 105a.

The sensor includes a sensing portion, such as sensing portion 132 shown in FIG. 3A that is disposed between a protective coating and a surface of the engineered structure 110. The sensor preferably has a physical construction of an electrode structure having interdigitated metal-based circuit formed on a flexible polyimide substrate.

At a particular sensor location, e.g., sensor 130a, the composite signal is demultiplexed by a demultiplexer, such as demultiplexer 137, into at least first and second optical signal components. A first optical signal component, such as the modulated $\lambda_1$ signal, can be converted into an electrical signal by the photo diode array 135, so that the resulting modulated electrical signal can power a modulating device, such as an electrochromic switch 136, at a selected frequency $\omega$. A second optical signal component, such as the $\lambda_2$ signal, passes through (or is optionally reflected by) the electrochromic switch 136, which modulates the $\lambda_2$ signal at the frequency $\omega$. As the modulating device is electrically coupled to the sensing portion of the sensor head, the state of the coating can influence the phase (or time delay) and amplitude of the modulated return $\lambda_2$ signal.

The now modulated optical signal $\lambda_2$ returns from the remote sensor via either a separate return signal fiber, such as fiber 107a, or the optical transmission line 105a and is received by the central controller. The returned optical signal $\lambda_2$ is converted to an electrical signal (t2) by a detector, such as detector 159. The converted return signal is then fed to a comparator, such as comparator circuit 155. Another electrical signal (t1), which is generated by the signal generator 157/modulator 153, corresponding to the amplitude modulating optical signal $\lambda_1$ is also fed to the comparator. The comparator measures the relative phase difference $\phi$ or time delay between the t2 signal and the t1 signal and the amplitude A of the optical signal $\lambda_2$ converted electrical signal $t_2$. Based on the phase difference and amplitude measurements, the optical response of the modulating device at the remote location that is measured while being powered by the PIN diode can be calculated as $P_1(\omega)=Ae^{(i\phi)}$.

Thus, the electrical impedance $R_C(\omega)$ of the sensor head and its immediate surroundings (including the coating 140 and the engineered structure 110 at that location) can thus be determined as follows:

$$R_C(\omega) = \frac{R_O(\omega)[P_0(\omega) - P_1(\omega)]}{P_1(\omega)} \quad (1)$$

where $R_O(\omega)$ is the initial impedance of the remote modulating device (as can be provided by the manufacturer or as can be measured prior to installation using standard EIS equipment), where $P_0(\omega)$ is the initial optical response of the remote modulating device measured while being powered by the PIN diode (prior to application of the coating and coupling the sensor head to the surface of the engineered structure), and where $P_1(\omega)=Ae^{(i\phi)}$, as is described above.

In order to provide a full spectroscopic measurement, the process described above is then repeated for different frequency values $\omega_1$ to $\omega_n$, so that amplitude and phase information is repeatedly gathered as a function of changing frequency. In practice, a range of frequencies from about 0.1 Hz to 1 MHz can provide suitable spectroscopic information.

Figure 4A:
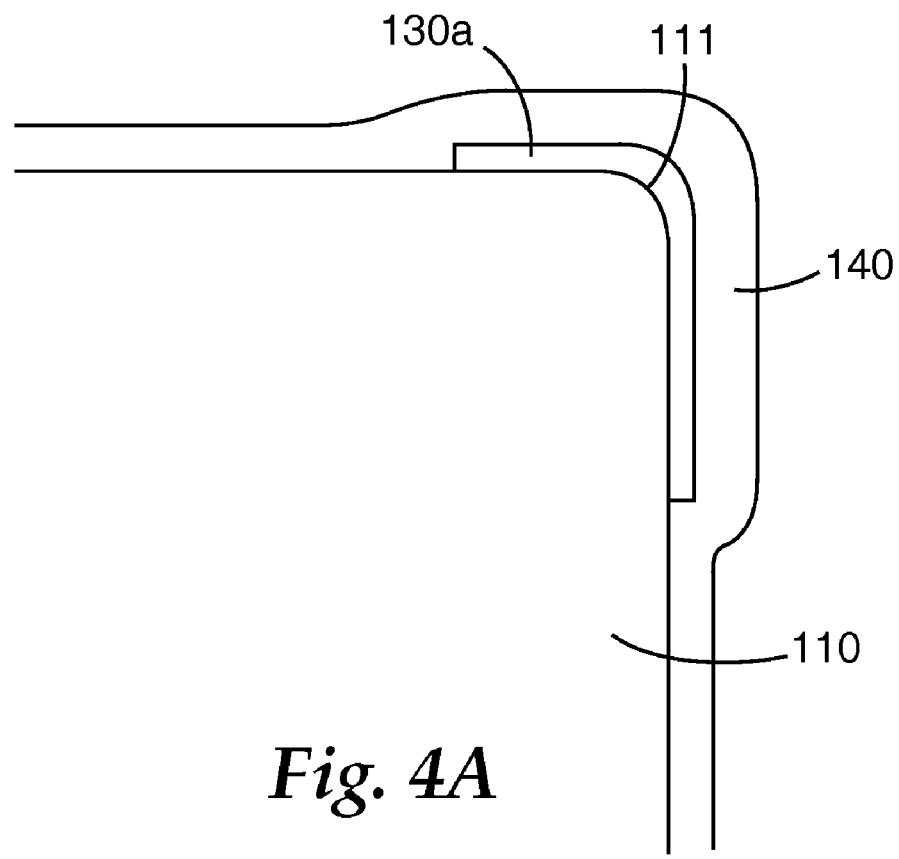
FIGS. 4A and 4B show alternative implementations of an exemplary sensor disposed on non-flat surfaces.
Figure 4B:
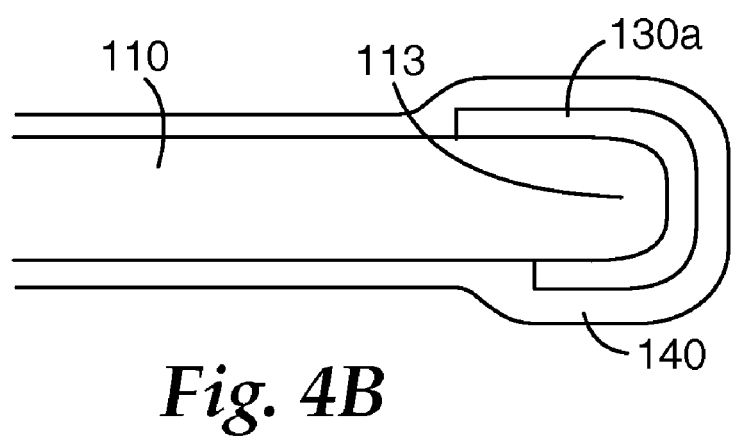

Using the above designs, exemplary embodiments of the detection system described herein can provide a non-disruptive, undercoating sensor. In addition, the sensors can be constructed on flexible, bendable substrates that allow a user to place sensors at critical areas of an engineered structure, such as non-flat surfaces (e.g., around bends and corners and other sharp-angled locations). These locations can be more susceptible to corrosion or other types of deteriorating events because protective coatings may not be evenly applied at corners and other sharp-angled locations. For example, as shown in FIGS. 4A and 4B, an exemplary sensor 130a can be disposed on a single corner surface 111 (FIG. 5A) or a multiple corner surface 113 (FIG. 5B) as might occur around the edge of an I-beam.

Thus, according to the above exemplary embodiments, embeddable corrosion sensors can be provided to detect real time impedance characteristics of the sensor head and its immediate surroundings (including the coating health and the structural health). As such sensors can be formed on flexible substrates, more location-specific real-time measurements can be provided to the user. Also, such thin circuits (e.g., ~0.001" thick) can be placed between a protective coating and the structure without adversely affecting the coating condition. Also, the data acquisition system can provide real time measurement of corrosion-related events. Such a corrosion sensor can help reduce the direct and indirect cost of corrosion related damage.

Experiments

Figure 6A:
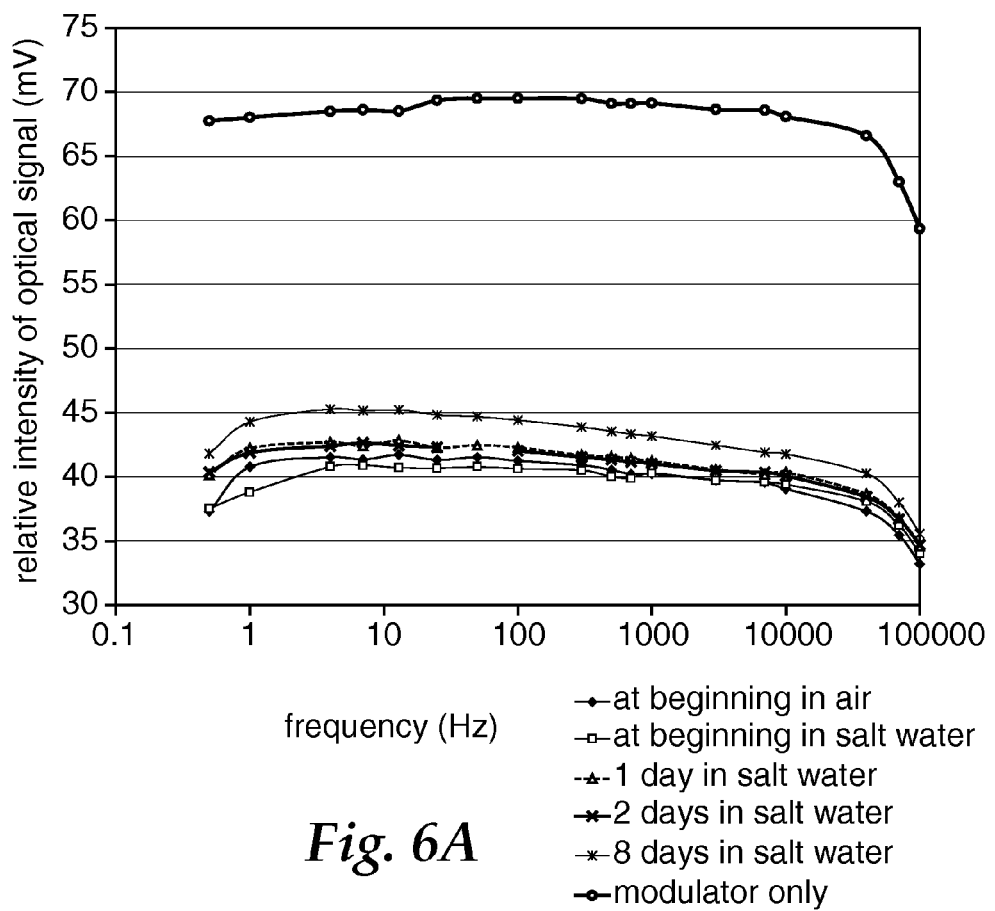
FIGS. 6A-6C show intensity, phase, and impedance results from a first set of experiments.
Figure 6B:
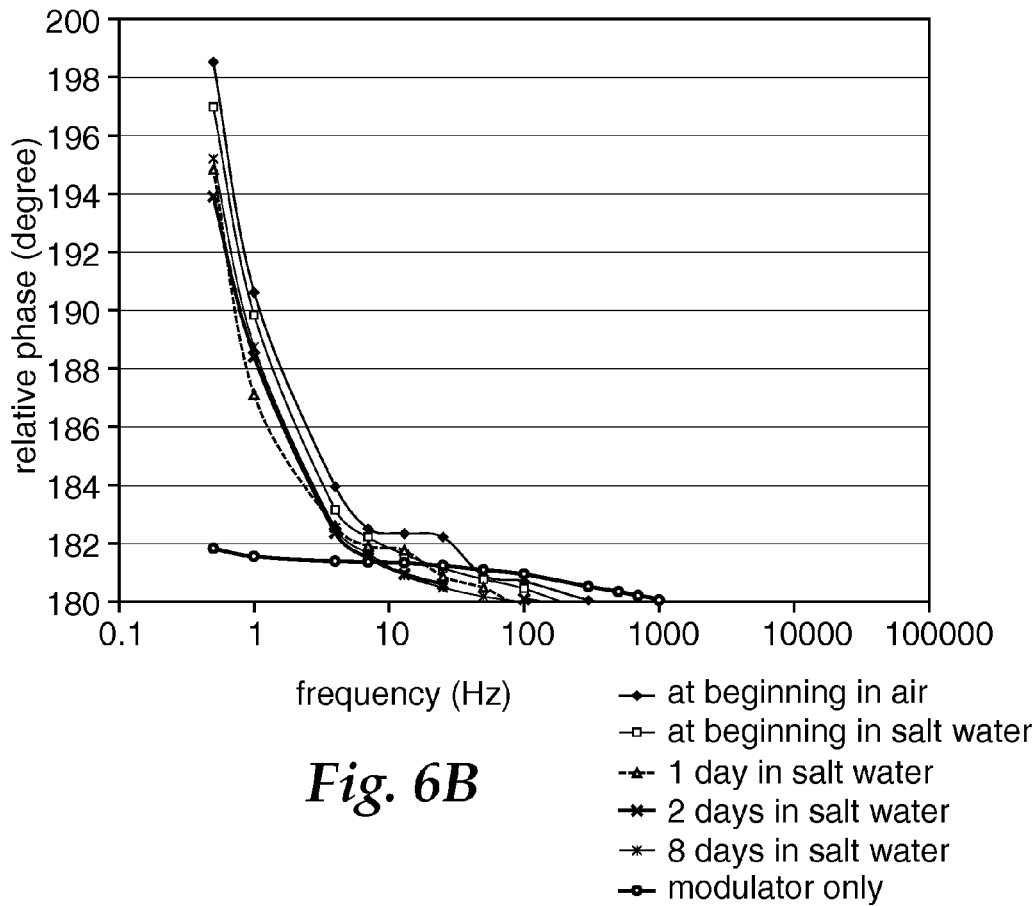
Figure 6C:
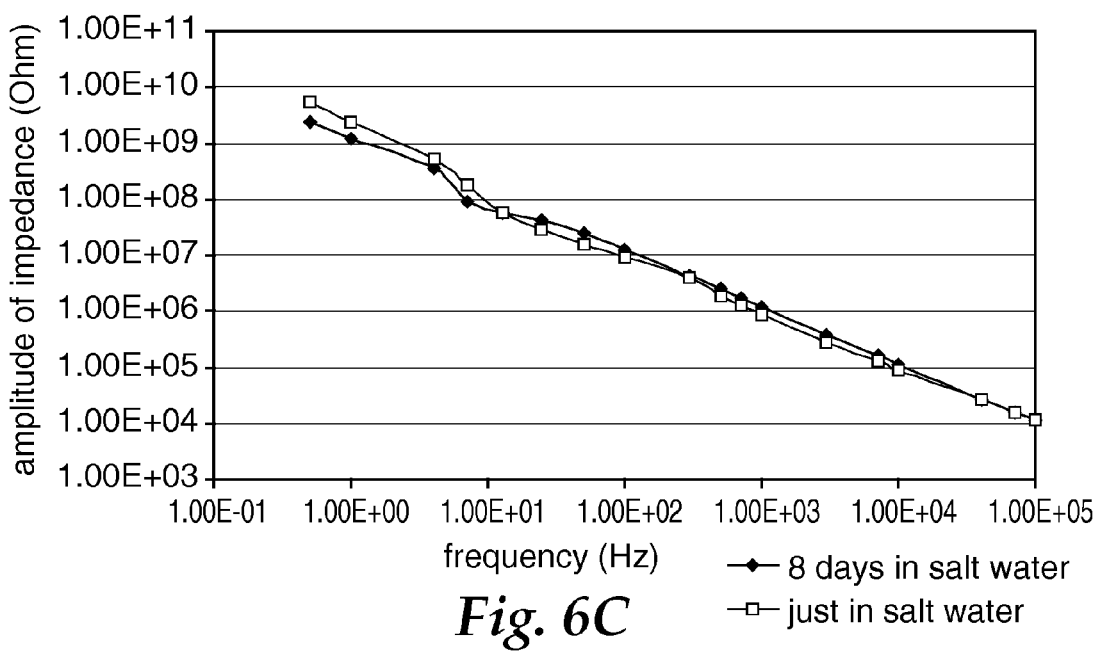

In a first experiment, the impedance of a sensor head (having a construction similar to that of sensor 132 described above) is measured. The sensor head was covered with an epoxy-based coating and was submerged in a bath of salt water. In particular, the sensor head was dip coated with about 5 mils of mil-spec 24441 epoxy coating, and was allowed to cure for 24 hours prior to submersion in a bath of artificial (ASTM) sea water. An AC signal powered the sensor head at a frequency $\omega$. In this experiment, instead of an electrochromic switch, a conventional lithium niobate modulator was utilized in its place. A 1.5 µm, continuous wave (or DC) optical signal was transmitted along a short length (3 m) of optical fiber (SMF-28 optical fiber, available from Corning, Inc.) through the modulator, which was placed in parallel with the sensor head. A photodiode converted the modulated return signal into an electrical signal. The (relative) intensity of the measured return signal (as a function of frequency $\omega$) and the relative phase of the return signal with respect to the phase of the AC power signal (as a function of frequency) is shown in FIGS. 6A and 6B. Several trials were employed and are detailed in the figure legends. The impedance was calculated for the sensor head (using the above equation $P_1(\omega)=Ae^{(i\phi)}$) and is shown in FIG. 6C (as a function of frequency). The figures for this experiment indicate a phase change and a relative increase in signal intensity with a deterioration of the coating.

In another experiment, comparative EIS tests were conducted, where an optical-based EIS measurement method, similar to that as is described in detail above, is compared to a standard EIS measurement. In both tests, the degradation of a specific coating, here an epoxy-based Mil-Spec 24441 coating was performed. A sensor head (having a construction similar to that of sensor 132 described above) was covered with the 24441 coating and was immersed in artificial (ASTM) sea-water. For the optical EIS test, a 1.5 µm, continuous wave (DC) optical signal was transmitted along a short length (3 m) of optical fiber (SMF-28 optical fiber, available from Corning, Inc.) through a lithium niobate modulator, which was placed in parallel with the sensor head. A photodiode converted the modulated return signal into an electrical signal.

Figure 7A:
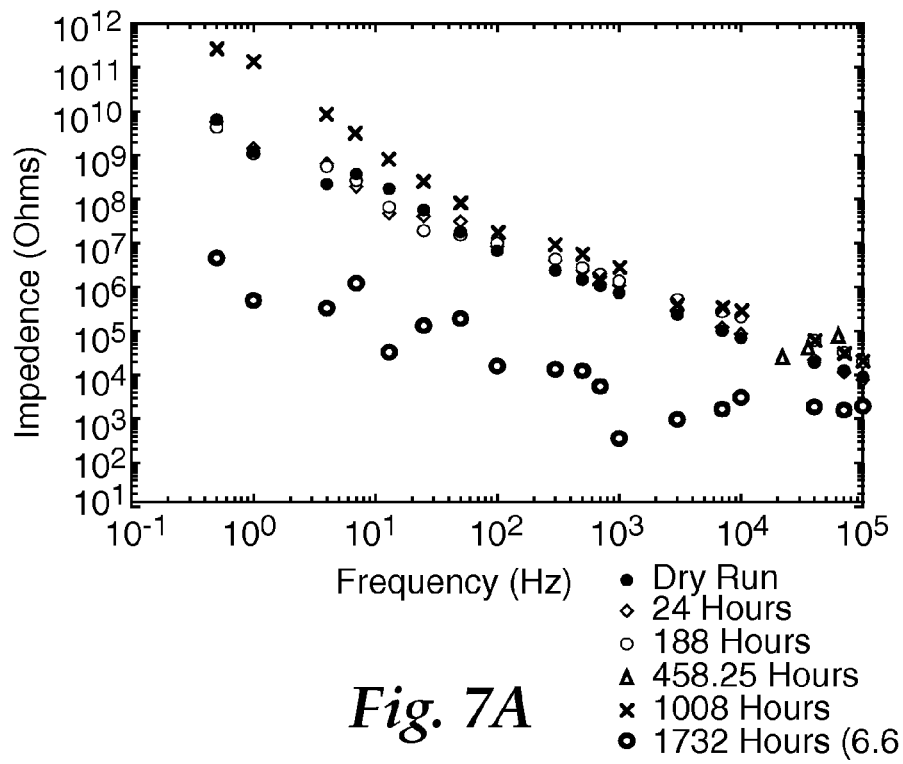
FIGS. 7A and 7B show impedance results from a second set of experiments.
Figure 7B:
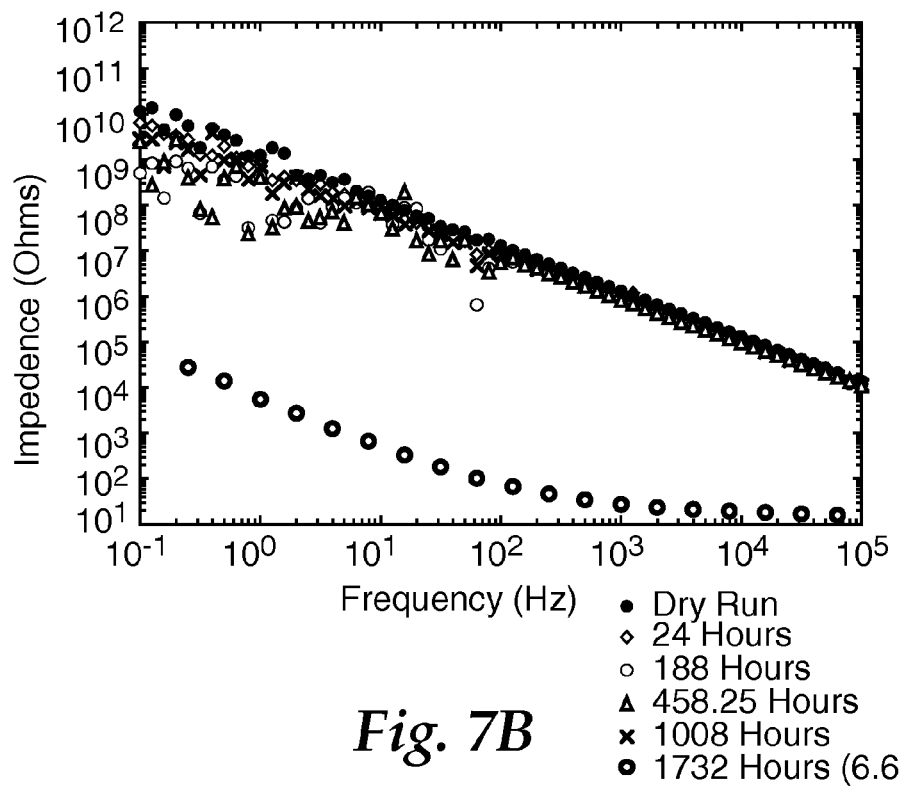

FIGS. 7A and 7B show the results of the optical-based and electrical based EIS measurements, respectively, where the impedance of the sensor is measured as a function of frequency. Several trials were employed and are detailed in the figure legends. Of note, the temperature of the bath was elevated after two days of immersion in order to accelerate the coating degradation. The multiple optical-based EIS impedance measurement (FIG. 7A) tracks similarly to the electrical-based EIS measurement (FIG. 7B). A difference in magnitude may be due to the estimated initial impedance value used for the modulator. However, both the optical EIS and electrical EIS measurements show an impedance drop of about 5 orders of magnitude over the frequency range.

Various modifications, equivalent processes, as well as numerous structures to which the present invention may be applicable will be readily apparent to those of skill in the art to which the present invention is directed upon review of the present specification.

What is claimed is:

1. A method of measuring the spectroscopic impedance of a sensor and its immediate surroundings, wherein the sensor is disposed on an engineered structure and is coated with a protective coating, comprising:
   providing a first optical signal having a first modulation frequency and amplitude;
   transmitting the first optical signal and a second optical signal from a first location to a sensor location;
   modulating the second optical signal with a second modulation frequency and amplitude, the second modulation frequency and amplitude converted from the first optical signal; and
   comparing the first modulation frequency to the second modulation frequency to determine one of a phase difference and a time lag and calculating the electrochemical impedance spectroscopy of the sensor and its immediate surroundings as a function of frequency.

2. The method of claim 1, wherein the transmitting step includes multiplexing the first optical signal with the second optical signal into a composite signal, the first optical signal being amplitude modulated and having a first wavelength, and the second optical signal being of continuous power and having a second wavelength different from the first wavelength.

3. The method of claim 1, wherein the modulating step includes modulating the second optical signal with a modulating device that is electrically connected to the sensor and that is powered by a signal that comprises an electrical conversion of the first optical signal.

4. The method of claim 2, further comprising splitting the composite optical signal into at least the first and second optical signals at the sensor location.

5. The method of claim 3, further comprising:
   transmitting the modulated second optical signal to the first location; and
   detecting the modulated second optical signal at the first location.

6. The method of claim 5, wherein the calculating step comprises calculating the electrochemical impedance spectroscopy of the sensor and its immediate surroundings from the following equation:

$$R_C(\omega) = \frac{R_O(\omega)[P_0(\omega) - P_1(\omega)]}{P_1(\omega)}$$

where $R_O(\omega)$ is an initial impedance of the modulating device, where $P_0(\omega)$ is an initial optical response of the modulating device at the sensor location, and where $P_1(\omega) = Ae^{(i\Phi)}$, where A is the amplitude of the modulated second signal as is detected at the first location and wherein $\phi$ is one of the phase difference and the time lag.

7. The method of claim 6, wherein the calculating step comprises calculating the electrochemical impedance spectroscopy over a range of frequencies from about 0.1 Hz to about 1 MHz.

8. A detection system for monitoring a physical condition of an engineered structure, comprising:
   a first sensor disposable on the engineered structure and disposable between a surface of the engineered structure and a protective coating substantially covering the surface, the first sensor including a modulation element;
   a controller for retrieving data from the sensors, the controller including a comparator circuit and a signal generator to provide an AC signal at a frequency $\omega$; and
   one or more optical fibers coupling an optical signal generated by the controller to the first sensor, wherein the first sensor provides electrochemical impedance data corresponding to the engineered structure and protective coating.

9. The detection system of claim 8, wherein the controller further comprises:
   a light source to generate the optical signal, wherein the optical signal comprises a first optical signal at a first wavelength having a first modulation frequency and amplitude, wherein the first modulation frequency and amplitude corresponds to the AC signal, and a second optical signal at a second wavelength, the second optical signal being of continuous power.

10. The detection system of claim 9, wherein the one or more optical fibers includes a first optical fiber to carry the first and second optical signals to the first sensor.

11. The detection system of claim 10, wherein the one or more optical fibers further comprises a second optical fiber to carry a return optical signal from the first sensor to the controller, the return optical signal comprising a modulated second optical signal, the second optical signal having a second modulation frequency and amplitude, the second modulation frequency and amplitude converted from the first optical signal.

12. The detection system of claim 9, wherein the controller further comprises:
   an optical multiplexer to combine the first and second optical signals into a composite signal, the first wavelength and the second wavelength being different.

13. The detection system of claim 9, wherein the sensor comprises:
   a sensor head having a patterned conductive element disposed on a flexible substrate mounted on the engineered structure and covered by a protective coating; and
   a modulating device electrically connected to the sensor head to receive the second optical signal.

14. The detection system of claim 13, wherein the sensor further comprises:
- an optical signal demultiplexer, wherein the demultiplexer sends the first optical signal along a second optical path and sends the second optical signal along a first optical path; and
- a photodiode array disposed on the second optical path to convert the first optical signal into an electrical signal, wherein the modulating device is disposed along the first optical path, and wherein the modulating device is powered by the electrical signal from the photodiode array.

15. The detection system of claim 14, wherein the modulating device comprises an electro-chromic switch.

16. The detection system of claim 8, wherein the controller further comprises a detector to receive and detect the return optical signal.

17. The detection system of claim 16, wherein the light source comprises first and second narrowband sources, wherein at least the first narrowband source is coupled to the signal generator.

18. The detection system of claim 8, wherein the engineered structure comprises one of a pipe and a girth weld portion of a pipe system.

19. The detection system of claim 8, further comprising a plurality of sensors coupled to the controller, wherein each sensor provides electrochemical impedance data corresponding to a particular portion of the engineered structure and its surrounding protective coating.

* * * * *